(12) United States Patent
Nakata

(10) Patent No.: US 8,888,705 B2
(45) Date of Patent: Nov. 18, 2014

(54) ULTRASOUND DIAGNOSIS APPARATUS

(75) Inventor: Kazuhito Nakata, Tochigi-ken (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 515 days.

(21) Appl. No.: 12/492,730

(22) Filed: Jun. 26, 2009

(65) Prior Publication Data

US 2010/0004541 A1  Jan. 7, 2010

(30) Foreign Application Priority Data

Jun. 26, 2008  (JP) ................. 2008-167948

(51) Int. Cl.
| | |
|---|---|
| G01S 7/52 | (2006.01) |
| G01S 15/89 | (2006.01) |
| A61B 8/13 | (2006.01) |
| A61B 8/08 | (2006.01) |
| A61B 8/06 | (2006.01) |

(52) U.S. Cl.
CPC ......... *G01S 15/8979* (2013.01); *G01S 7/52095* (2013.01); *G01S 15/8993* (2013.01); *A61B 8/13* (2013.01); *A61B 8/483* (2013.01); *A61B 8/06* (2013.01); *G01S 7/52085* (2013.01)
USPC ........................... 600/443; 600/441; 600/447

(58) Field of Classification Search
USPC .................... 600/437, 441, 443, 444
See application file for complete search history.

(56) References Cited

U.S. PATENT DOCUMENTS

| | | | | |
|---|---|---|---|---|
| 5,793,701 A | * | 8/1998 | Wright et al. ................ 367/7 |
| 6,374,674 B1 | | 4/2002 | Mine | |
| 6,471,650 B2 | * | 10/2002 | Powers et al. ............ 600/447 |
| 6,482,157 B2 | * | 11/2002 | Robinson .................. 600/437 |
| 2002/0144549 A1 | * | 10/2002 | Yao ............................. 73/602 |
| 2003/0032882 A1 | * | 2/2003 | Mochizuki ................ 600/443 |
| 2005/0101864 A1 | * | 5/2005 | Zheng et al. .............. 600/443 |
| 2009/0043208 A1 | * | 2/2009 | Hergum et al. ........... 600/455 |
| 2009/0306510 A1 | * | 12/2009 | Hashiba et al. ........... 600/447 |
| 2010/0022890 A1 | * | 1/2010 | Fukukita et al. .......... 600/459 |

FOREIGN PATENT DOCUMENTS

| | | | |
|---|---|---|---|
| JP | 3-155843 | | 7/1991 |
| JP | 4-254754 | | 9/1992 |
| JP | 2000-116651 | | 4/2000 |
| JP | PCT/JP2006/301404 | * | 1/2006 |
| JP | 2008-73085 | | 4/2008 |
| JP | 2008-251125 | | 9/2008 |
| WO | WO 2005/115250 A1 | | 12/2005 |

OTHER PUBLICATIONS

U.S. Appl. No. 12/568,110, filed Sep. 28, 2009, Nakata.
Notice of Rejection Reasons issued Jan. 25, 2013 in Japanese Patent Application No. 2008-167948 (with English translation).
Office Action issued on Jan. 10, 2014 in the corresponding Japanese Patent Application No. 2008-167948 (with English Translation).

* cited by examiner

*Primary Examiner* — Christopher Cook
(74) *Attorney, Agent, or Firm* — Oblon, Spivak, McClelland, Maier & Neustadt, L.L.P.

(57) ABSTRACT

An ultrasound diagnosis apparatus that can generate and display 3D ultrasound image data of superior image quality in real time is provided. To achieve a high volume rate for acquiring 3D ultrasound image data, the ultrasound diagnosis apparatus performs 3D scans on a 3D region of an object while sequentially shifting a transmission/reception group that is comprised of each of the transmitting acoustic fields and more than five parallel simultaneous reception beam directions corresponded to each of the transmitting acoustic fields at a prescribed angular distance $\Delta\xi_0$ along the $\theta$ (azimuth) direction and the $\phi$ (elevation) direction.

7 Claims, 11 Drawing Sheets

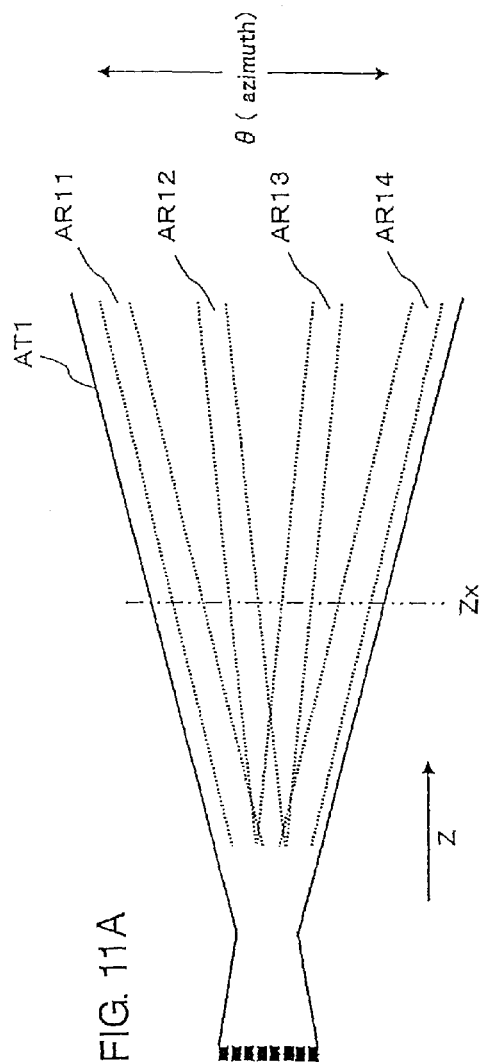
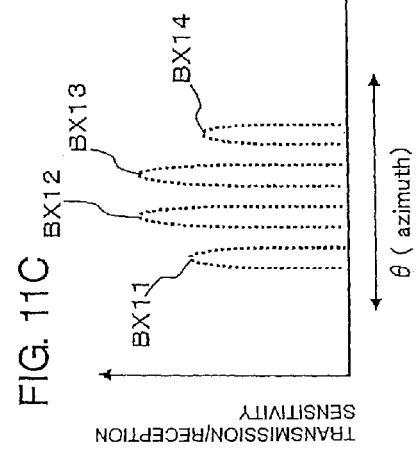
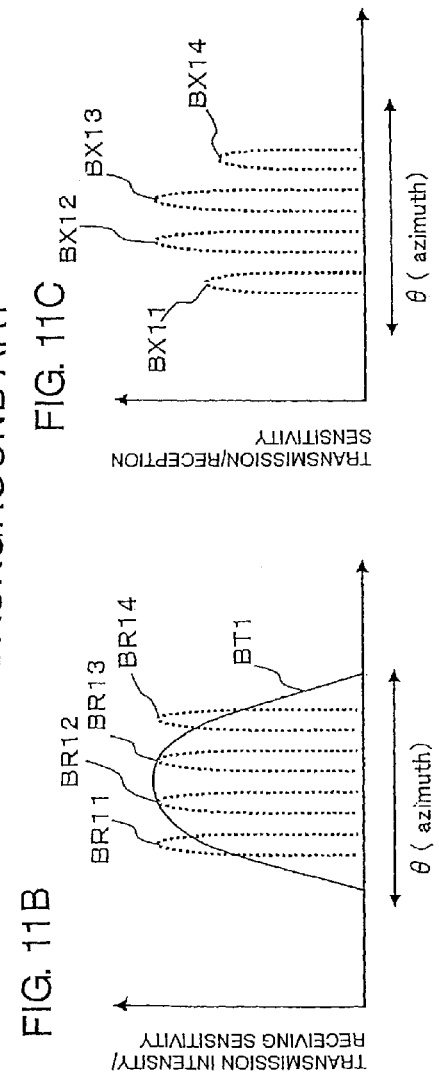
FIG. 11A
FIG. 11B
FIG. 11C
BACKGROUND ART

ULTRASOUND DIAGNOSIS APPARATUS

CROSS-REFERENCE TO RELATED APPLICATIONS

This application claims priority from, and the benefit of, Japanese Patent Application No. 2008-167948, filed on Jun. 26, 2008, the contents of which are expressly incorporated herein by reference in their entirety.

BACKGROUND OF THE INVENTION

A. Field of the Invention

The present invention relates to an ultrasound diagnosis apparatus for displaying 3-dimensional (3D) images by performing a 3D scan over a target region by using a 2-dimensional (2D) array ultrasound probe. More particularly, the present invention relates to a parallel simultaneous reception-type ultrasound diagnosis apparatus that can acquire 3D image data (hereinafter, "volume data") with an increased acquisition rate of 3D ultrasound image data (volume rate) by eliminating heterogeneous sensitivities among parallel simultaneous receiving beams.

B. Background of the Invention

An ultrasound image diagnosis apparatus transmits and receives ultrasound through a plurality of ultrasound transducers installed in an ultrasound probe to and from a target in an object in a plurality of directions in order to display the image of the target on a monitor. Since an ultrasound image diagnosis apparatus can easily obtain and display a 2D image or a 3D image in real time by simply touching an ultrasound probe to a patient's body surface, it is widely used as an apparatus for diagnosing the status of a target organ in a patient's body.

In particular, displays of B mode image data acquired by using an ultrasound pulse reflection method and color Doppler image data acquired by using an ultrasound image Doppler method are inevitable for an ultrasound image diagnosis for tissues and blood cells in a living body.

Generally, an electronic scan-type ultrasound diagnosis apparatus uses a plurality of transducers arranged in a line and displays 2D image data in real time by electrically controlling the drives of the plurality of transducers at a high speed. The 2D image data is generated by performing 2D scans over an object. Recent years, it has become possible to utilize an ultrasound diagnosis apparatus that can generates 3D image data at an optional cross-section, such as 2D image data (Multi-Planar Reconstruction (MPR) image data) or volume rendering image data by performing 3D scans and to acquire wide range data of a 3D region of an object in a short time.

To acquire the volume data, there are two kinds of acquiring methods. One is a mechanical data acquisition method that moves or rotates a conventional ultrasound probe including linearly arranged transducers. The other is an electronic data acquisition method that electronically controls driving signals for a plurality of transducers arranged in a 2D array and also electronically controls receiving signals acquired through the 2D array transducers. While a mechanical data acquisition type ultrasound diagnosis apparatus is relatively easy to construct, it needs a lot of time for acquiring volume data. Accordingly, it is very difficult for the mechanical data acquisition type ultrasound diagnosis apparatus to correctly acquire data of quickly moving organs or blood flow. On the contrary, although an ultrasound probe and a main body for an electrically data acquisition type ultrasound diagnosis apparatus requires complex constructions, it can acquire volume data in a short time. In particular, with accompanying a 3D scan synchronized with heart beats (triggered volume scan), it becomes possible to display 3D image data of a quick moving organ, i.e., a heart, as motion pictures.

However, while the triggered volume scan is effective to the diagnosis for a circulation organ, it can not to apply to an object having a severe arrhythmia. Further, since a blood flow measurement under the ultrasound Doppler method requires a plurality of ultrasound transmissions and receptions on the same portion in order to acquire the flood speed data, it becomes difficult to display 3D color Doppler image data in real time.

In order to improve acquisition speed of the volume data, it has been proposed to apply the parallel simultaneous reception method for simultaneously receiving echo signals from a plurality of directions (For instance, Japanese Patent Application Publication 2000-116651). FIG. 9 explains the 4-beams parallel simultaneous reception method by using a 2D array ultrasound probe in which a plurality of transducers are arranged both in the θ (azimuth) direction and the φ (elevation) direction. The 4-beams parallel simultaneous reception is performed by 2 beams parallel simultaneous reception both in the θ (azimuth) direction and the φ (elevation) direction for each transmission beam region (hereinafter, "transmitting acoustic field"). For instance, in the transmitting acoustic field T1 having a transmitting beam center axis (●) C1, 2 beams parallel simultaneous receptions in the θ (azimuth) direction and 2 rows parallel simultaneous receptions in the φ (elevation) direction are performed. Thus, 4 reception beam directions (○) R1, R2, R3, and R4 are received from the transmitting acoustic field T1 as one receiving group.

According to the conventional 4-beams parallel simultaneous reception method, as illustrated in FIG. 9, a plurality of transmitting acoustic fields T1, T2, . . . , Tn is set on a 3D region of an object so as to be located at a prescribed angular distance $\Delta\xi_0$ from each other. Further, in each transmitting acoustic field, for instance T1, each of the parallel simultaneous reception 4 beams, for instance R1, R2, R3, and R4 is set at an equal direction of an angular distance $\Delta\xi$ apart from a beam center axis C1 of the transmitting acoustic field T1 so as to obtain an equal transmission intensity to each of the parallel simultaneous reception 4 beams. Consequently, a transmission/reception sensitivity that is decided by a product of the transmission intensity and the reception sensitivity is also equal to each of the parallel simultaneous reception 4 beams in each transmitting acoustic field. Thus, by performing 3D scans in accordance with the 4-beams parallel simultaneous reception method, 3D ultrasound image data (volume data) can be acquired with a small unevenness of sensitivity among the 4 receiving beams.

However, when the number of the receiving beams for the parallel simultaneous reception is increased to more than five (5) in order to increase an acquisition rate of the volume data (volume rate), it becomes impossible to obtain equal transmission/reception sensitivity by applying the conventional parallel simultaneous reception method. Thus, problems of sensitivity unevenness and sensitivity differences would occur.

FIG. 10 illustrates a case that the number of the receiving beams for the parallel simultaneous reception is increased to eight (8) in the conventional parallel simultaneous reception method. To perform 8 beams parallel simultaneous reception, 4 receiving beams arranged in the θ (azimuth) direction and 2 rows of the 4 receiving beams in the φ (elevation) direction are received as one group of the parallel simultaneous reception beams. Thus, two rows of 4 parallel simultaneous reception beams are set against a transmitting acoustic field. For instance, parallel simultaneous reception 8 beams R11 to R18 are set to a transmitting acoustic field T1 having a center axis C1 as setting 4 beams in the θ (azimuth) direction and 2 rows in the φ (elevation) direction. In this case, as shown in FIG. 10, a first angular distance $\Delta\xi1$ between the center axis C1 of the transmitting acoustic field T1 and each of the parallel simultaneous reception 4 beams R11, R14, R15, and R18 that are located at a far-off position from the center axis C1 becomes larger than a second angular distance $\Delta\xi2$ between the center axis C1 of the transmitting acoustic field T1 and each of another parallel simultaneous reception 4 beams R12, R13, R16, and R17 that are located near to the center axis C1 in the transmitting acoustic field T1. Consequently, the transmission/reception sensitivity for each of the parallel simultaneous reception 4 beams R11, R14, R15, and R18 becomes lower than the transmission/reception sensitivity for the parallel simultaneous reception 4 beams R12, R13, R16, and R17 that are located near to the center axis C1 in the transmitting acoustic field T1.

FIG. 11A is a model for illustrating a relationship between the transmitting acoustic field AT1 having a center axis C1 shown in FIG. 10 and each of reception beam regions (acoustic fields) AR11 to AR14 of the parallel simultaneous reception beams R11, R12, R13, and R14 corresponding to the transmitting acoustic field AT1. A beam width of the transmitting acoustic field AT1 is set so as to be larger than each beam width of the receiving acoustic fields AR11 to AR14 in order to acquire sufficient transmission/reception sensitivities for all of the parallel simultaneous reception beams R11 to R14.

FIG. 11B illustrates a transmission intensity distribution BT1 of the transmitting acoustic field AT1 at a cross-section Zx orthogonally crossing the center axis (z axis) shown in FIG. 11A and reception sensitivity distributions BR11 to BR14 for the parallel simultaneous reception 4 beams. FIG. 11C illustrates each of the transmission/reception sensitivity distributions BX11 to BX14 of the parallel simultaneous reception 4 beams R11 to R14 that is respectively calculated as a product of the transmission intensity distribution BT1 shown in FIG. 11B and each of the reception sensitivity distributions BR11 to BR14.

As apparent from the transmission/reception sensitivity distributions shown in FIG. 11C, sensitivity differences occur among the transmission/reception sensitivities BX12, BX13 for the reception beams locating near to the transmitting acoustic field center axis and the transmission/reception sensitivities BX11, BX14 of the reception beams locating far apart from the transmitting acoustic field center axis. Thus, when the number of parallel simultaneous reception beams are increased to 8 by applying the conventional parallel simultaneous reception, transmission/reception sensitivity differences would be generated depending upon the angular distances between the transmitting acoustic field center axis and each of the parallel simultaneous reception beam directions. This causes a non-permissible problem of sensitivity unevenness in the acquired volume data. To reduce such unevenness of the transmission/reception sensitivity, it is intended to expand the beam width of the transmission beam. However, by doing so, the transmission intensity distribution BT1 is also reduced. Consequently, the transmission/reception sensitivities for each of the reception beams are deteriorated. This causes another problem of a deterioration of the S/N ratio for the volume data.

SUMMARY OF THE INVENTION

The present invention solves the above-mentioned conventional problems and defects, and provides an ultrasound diagnosis apparatus that can acquire 3D ultrasound image volume data in a short time while avoiding deterioration of the transmission/reception sensitivity and the sensitivity unevenness. According to the ultrasound diagnosis apparatus consistent with the present invention, the number of the parallel simultaneous reception beams can be increased to more than 5 in order to increase a volume data acquisition speed (volume rate). Further, it is possible to avoid the sensitivity unevenness among the parallel simultaneous reception beams and to improve the S/N ratio for the volume data.

The ultrasound diagnosis apparatus according to one embodiment of the present invention is configured to generate 3D ultrasound image data based on ultrasound receiving signals acquired through 3D scans using a parallel simultaneous reception method, the ultrasound diagnosis apparatus comprising:

(1) a scan control unit configured to set an ultrasound transmitting acoustic field and a plurality of parallel simultaneous reception beam directions corresponding to a center axis of the transmitting acoustic field and to perform the 3D scans by sequentially shifting the transmitting acoustic field and the plurality of parallel simultaneous reception beam directions corresponded to the transmitting acoustic field along a prescribed direction;

(2) an ultrasound probe including a plurality of 2D array transducers;

(3) a transmission unit configured to emit an ultrasound transmission beam by driving the plurality of transducers;

(4) a reception unit configured to perform parallel simultaneous reception of the ultrasound receiving signals of a plurality of channels acquired through each of the plurality of parallel simultaneous reception beam directionsd, respectively; and (5) an image data generating unit configured to generate ultrasound image data based on the delayed and summed ultrasound receiving signals acquired from each of the parallel simultaneous reception beam directions that are sequentially shifted to the prescribed direction, wherein the scan control unit sets, as the plurality of parallel simultaneous reception beam directions more than spaced 5 parallel simultaneous reception beam directions, that are spaced equally apart from the center axis of the ultrasound transmitting acoustic field.

The ultrasound diagnosis apparatus according to another embodiment of the present invention is configured to generate image data based on ultrasound receiving signals acquired through 3D scans using a parallel simultaneous reception method, the ultrasound diagnosis apparatus comprising:

(1) a scan control unit configured to set an ultrasound transmitting acoustic field and 8 parallel simultaneous reception beam directions that are spaced apart from the transmitting acoustic field at a prescribed angular distance or at a prescribed distance, and to perform the 3D scans by sequentially shifting the transmitting acoustic field and the parallel simultaneous reception beam directions in a prescribed direction;

(2) an ultrasound probe including a plurality of 2D array transducers;

(3) a transmission unit configured to emit transmission ultrasounds for forming the transmitting acoustic field by driving the plurality of transducers;

(4) a reception unit configured to achieve parallel simultaneous reception by delaying and summing the ultrasound receiving signals of a plurality of channels acquired from each of the parallel simultaneous reception beam directions; and (5) an image data generating unit configured to generate ultrasound image data based on the delayed and summed ultrasound receiving signals acquired from each of the parallel simultaneous reception beam directions sequentially shifted to the prescribed direction, wherein the scan control unit sets the parallel simultaneous reception beam directions that are acquired through the 3D scan around the transmission beam directions so as that the reception beam directions are located at equal distances to two orthogonal crossing directions by shifting the parallel simultaneous reception beam direction.

The ultrasound diagnosis apparatus according to embodiments of the present invention performs ultrasound parallel simultaneous reception by a transmitting acoustic field having a relative larger beam width and a plurality of reception beams, each having a uniform thin beam width, that are spaced apart a prescribed angular distance $\Delta\xi$ from a center axis of the transmitting acoustic field. The ultrasound diagnosis apparatus according to the present invention further performs 3D scans on a 3D region of an object by sequentially shifting a transmission/reception group that is comprised of each of the transmitting acoustic fields and more than five (5) parallel simultaneous reception beams corresponded to each of the transmitting acoustic field, at a prescribed of angular distance $\Delta\xi_0$ along the $\theta$ (azimuth) direction and the $\phi$ (elevation) direction. According to the ultrasound diagnosis apparatus consistent with the present invention, it becomes possible to generate and display a 3D ultrasound image data of superior image quality in real time.

BRIEF DESCRIPTION OF THE DRAWINGS

The accompanying drawings, which are incorporated in and constitute part of this specification, illustrate various embodiments and/or features of embodiments of the present invention, and together with the description, serve to explain embodiments of the present invention. Where possible, the same reference number will be used throughout the drawings to describe the same or like parts. In the drawings:

FIG. 11A illustrates relationship between the transmission beam and the reception beams shown in FIG. 10;

FIG. 11B illustrates the transmission intensity distribution formed by the transmission beam and the reception sensitivity distributions formed by the parallel simultaneous reception beams shown in FIG. 10; and FIG. 11C illustrates the unevenness among the transmission/reception sensitivity distributions based on the transmission intensity distribution and the reception sensitivity distributions shown in FIG. 11B.

DESCRIPTION OF THE EMBODIMENTS

According to embodiments of the present invention, 3D ultrasound volume data of an even transmission/reception sensitivity to a 3D region in an object can be acquired in a short time by sequentially shifting a transmission/reception group of the transmitting acoustic field and the plurality of parallel simultaneous reception beam directions at a prescribed of angular distance $\Delta\xi_0$ in the $\theta$ (azimuth) direction and the $\phi$ (elevation) direction with setting more than five (5) parallel simultaneous reception beam directions corresponding to each of the transmitting acoustic fields that have a relatively larger beam width at a prescribed of angular distance $\Delta\xi_0$ along the $\theta$ (azimuth) direction and the $\phi$ (elevation) direction on a circle.

In the following embodiment of the ultrasound diagnosis apparatus consistent with the present invention, a sector scan type ultrasound diagnosis apparatus is explained so as to apply the parallel simultaneous reception method. The invention can apply to a linear scan type or a convex scan type ultrasound diagnosis apparatus.

Figure 1:
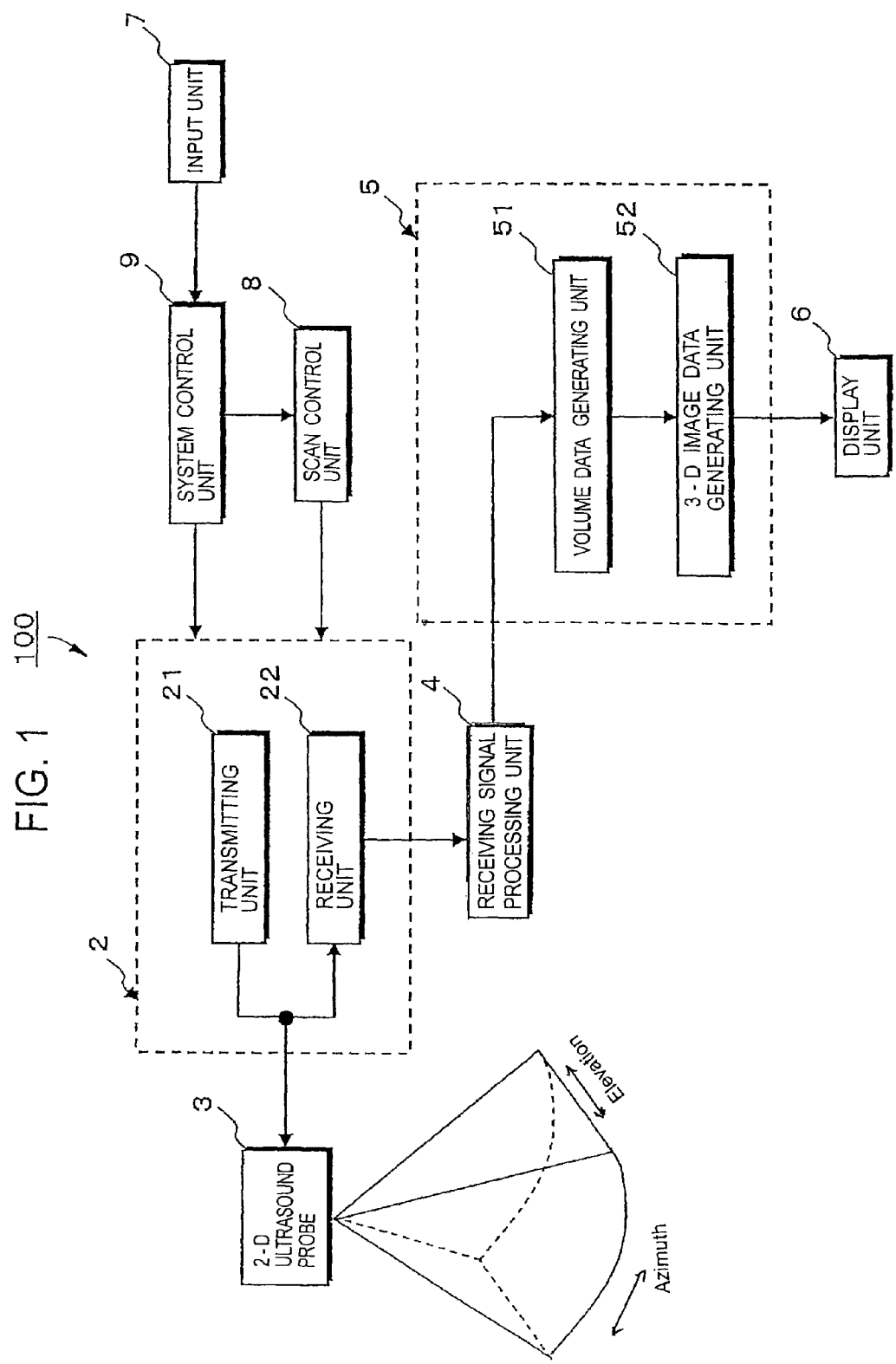
FIG. 1 is a block diagram illustrating an ultrasound diagnosis apparatus in accordance with preferred embodiments of the present invention.

FIG. 1 is a block diagram illustrating an ultrasound diagnosis apparatus in accordance with preferred embodiments of the present invention. The ultrasound diagnosis apparatus 100 is comprised of an ultrasound probe 3, a transmission/reception unit 2, a receiving signal processing unit, and an image data generating unit 5. The ultrasound probe 3 includes a plurality of transducers for transmitting ultrasound pulses (transmitting ultrasound signals) to a 3D region of a diagnosis target in an object and for converting reflected ultrasound signals to electric receiving signals. The transmission/reception unit 2 supplies driving signals to the plurality of transducers in the ultrasound probe 3 for transmitting ultrasounds to prescribed directions in the 3D region, and performs delaying and summing the ultrasound receiving signals of a plurality of channels acquired through each of the plurality of transducers. The receiving signal processing unit 4 generates B mode data and color Doppler data by processing the delayed and summed receiving signals. The image data generating unit 5 generates 3D image data based on the B mode data and color Doppler data acquired by performing a 3D scan over a diagnosis target portion.

The ultrasound diagnosis apparatus 100 further includes a display unit 6 for displaying the generated 3D image data; an input unit 7 for performing input operations, such as an input of object data, setting for image data generating conditions or image data displaying conditions, and inputs of various command signals; a scan control unit 8 for controlling 3D scans on the object by setting transmission delay times and reception delay times in the transmission/reception unit 2; and a system control unit 9 for overall control of the above-mentioned units.

In a tip portion of the ultrasound probe 3, a plurality $N_0$ of transducers are arranged in 2 dimensions. Each of the transducers is coupled to input/output terminals of the transmission/reception unit 2 through a cable having $N_0$ channels. Each of the transducers converts driving signals to ultrasound pulses in transmission times and converts echo ultrasounds to receiving signals in reception times.

In the present embodiment, an ultrasound probe 3 is explained as a sector scanning ultrasound probe having a plurality $N_0$ transducers arranged in 2 dimensions. Among the plurality $N_0$ of transducers, $N_t$ of the transducers are preliminary set as transmitting transducers groups and $N_r$ transducers in the plurality $N_0$ of transducers are preliminary set as receiving transducer groups. Each of the transducers in the transmitting transducer groups emits transmission ultrasounds into an object by being driven with $N_t$ channel driving signals supplied from the transmission/reception unit 2. Echo ultrasounds acquired from the object corresponding to the transmission ultrasounds are converted to $N_r$ channel receiving signals through the receiving transducer groups.

Figure 2:
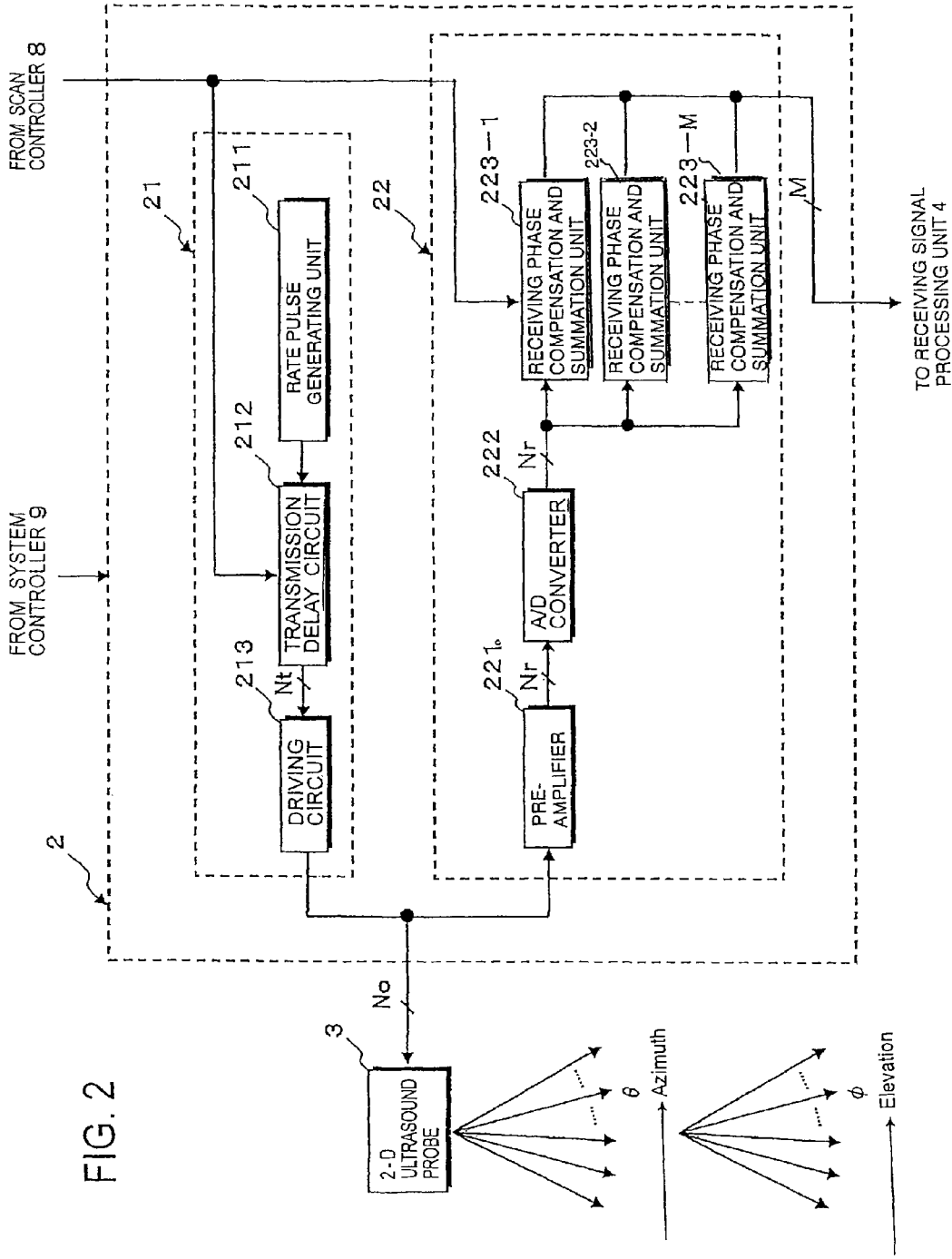
FIG. 2 is a block diagram illustrating the transmission and reception unit in the ultrasound diagnosis apparatus shown in FIG. 1.

FIG. 2 is a block diagram illustrating a construction of the transmission/reception unit 2 included in the ultrasound diagnosis apparatus shown in FIG. 1. The transmission/reception unit 2 includes a transmission unit 21 and a reception unit 22. The transmission unit 21 supplies driving signals to the transmitting transducers $N_t$ provided in the ultrasound probe 3 for emitting transmission ultrasounds to an object. The reception unit 22 performs delayed and summed the $N_r$ channel receiving signals acquired through the receiving transducers $N_r$ in the ultrasound probe 3.

The transmission unit 21 includes a rate pulse generating unit 211, a transmission delay circuit 212, and a plurality ($N_t$) of channels of driving circuit 213. The rate pulse generator 211 generates the rate pulses for determining a repetition cycle of the transmission ultrasounds by dividing a reference signal supplied from the system control unit 9. The transmission delay circuit 212 is comprised of a plurality of (Nt) channels of independent delay circuits and gives the focusing delay times for focusing the transmission ultrasound at a prescribed depth distance, and the deflecting delay times for emitting transmission ultrasound to the generated rate pulse. The driving circuit 213 generates driving pulses for driving the plurality ($N_t$) of transmitting transducers based on the delayed rate pulse.

The reception unit 22 includes a pre-amplifier 221, an A/D converter 222 converting $N_r$ channels, and receiving delay and summation units (beam formers) having M channels 223-1 to 223-M. The pre-amplifier 221 amplifies the receiving signals of $N_r$ channels supplied from the receiving transducers in the ultrasound probe 3 in order to keep a sufficient S/N ratio. The pre-amplifier 221 includes a limiter circuit (not shown) at the first stage of the pre-amplifier for protecting the pre-amplifier from the driving signals of high voltages generated by the driving circuit 213 in the transmission unit 21.

The receiving signals of $N_r$ channels acquired through the receiving transducers are amplified to a prescribed amplitude in the pre-amplifier 221 and converted to digital signals by the A/D converter 222. The converted digital signals are supplied to each of the receiving delay and summation units 223-1 to 223-M.

Each of the receiving delay and summation units 223-1 to 223-M includes a reception delay circuit and a summation circuit (not shown) for summing to the receiving signals of Nr channels converted to the digital signals by the A/D converter 222 by providing deflection delay times for setting a strong receiving directivity to each of the plurality of parallel simultaneous reception beam directions located in the transmission beam acoustic field, and by providing the focusing delay times for focusing the reception ultrasounds from a prescribed depth. In this case, the reception beams having substantially uniform thin beam width are formed to the ultrasound transmission/reception beams by renewing the focusing delay time, or both of the focusing delay time and the number of the reception channel in accompanying to the reception time by applying a so-called dynamic focusing method that sequentially moves a focus region of the reception beam from a shallow region to a deep region.

Figure 3:
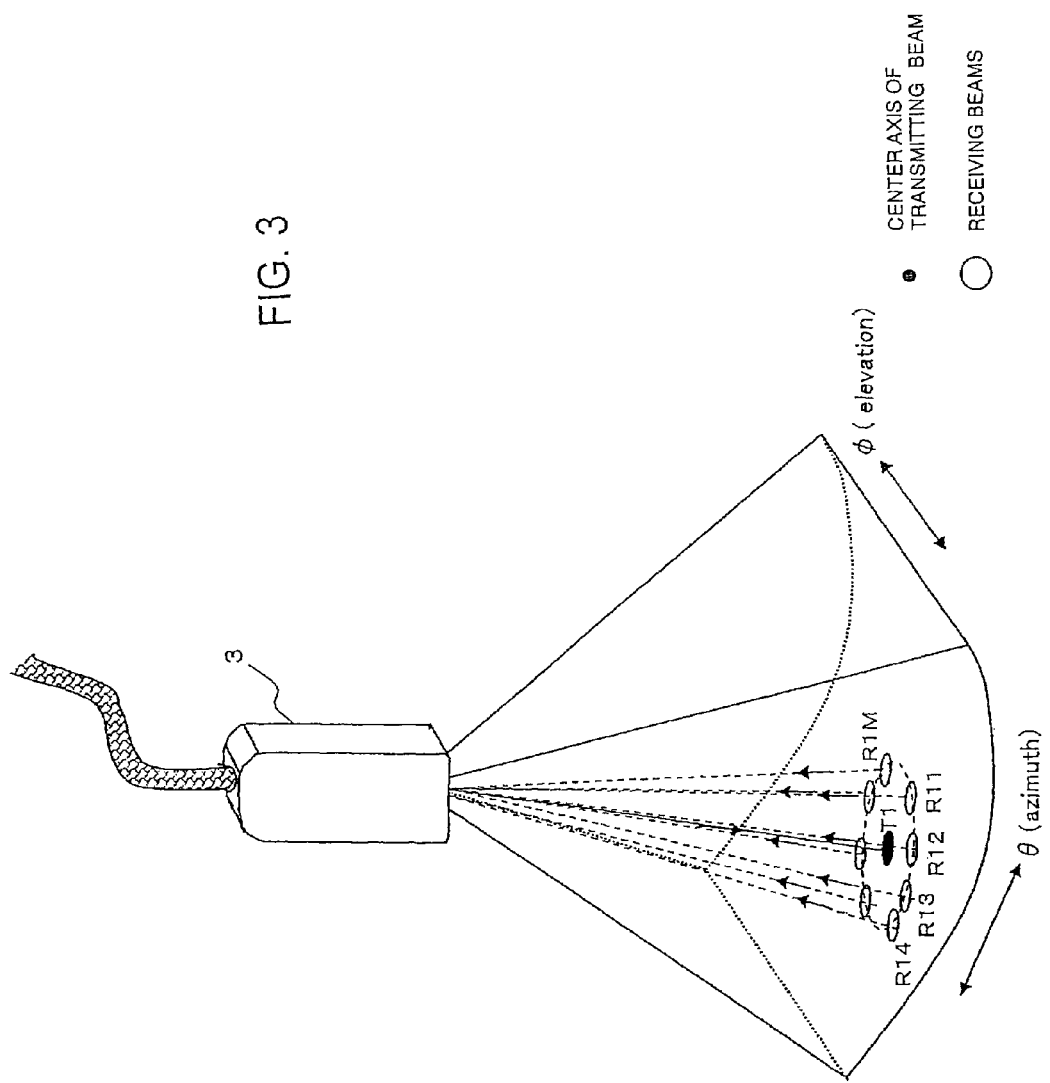
FIG. 3 is a model for illustrating the parallel simultaneous receptions by using a 2D array ultrasound probe in an ultrasound diagnosis apparatus shown in FIG. 1.

FIG. 3 illustrates a transmission beam acoustic field T1 emitted from the ultrasound probe 3 and a plurality of parallel simultaneous reception beams R11 to R1M (M=8) set around the transmission beam acoustic field T1. The 8-direction parallel simultaneous reception beams R11 to R18 are set at an equal angular distance to the transmission beam acoustic field T1 so that the transmission/reception sensitivity remains uniform. The details would be explained later.

Figure 4:
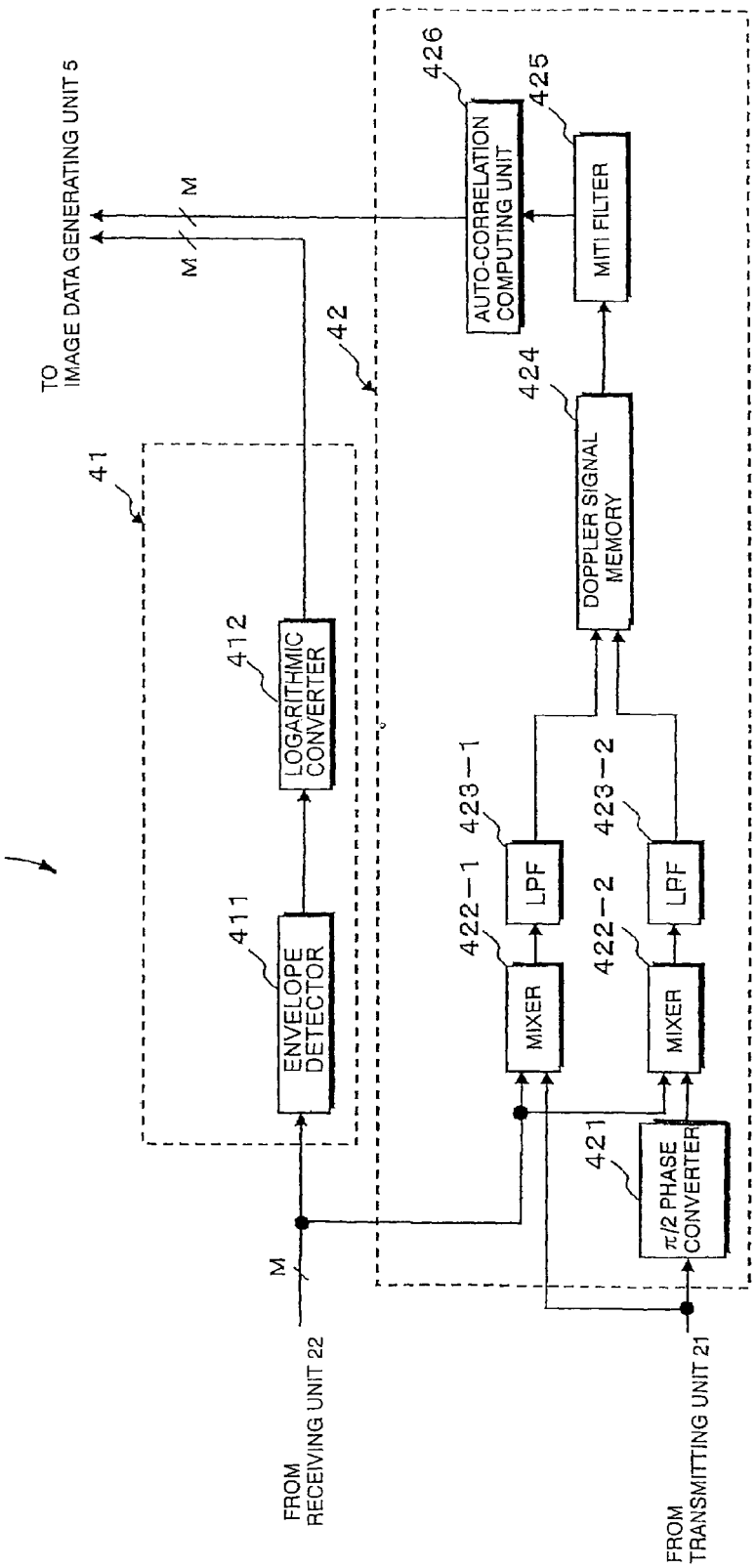
FIG. 4 is a block diagram illustrating the receiving signal processing unit in the ultrasound diagnosis apparatus shown in FIG. 1.

FIG. 4 illustrates a construction of the receiving signal processing unit 4 provided in the ultrasound diagnosis apparatus shown in FIG. 1. The receiving signal processing unit 4 includes a B mode data generating unit 41 for generating B mode data by processing the phase delayed and summed receiving signals of M channels outputted from the receiving delay and summation units 223-1 to 223-M in the reception unit 22, and a color Doppler data generating unit 42 for generating color Doppler data by processing the receiving signals of M channels.

The B mode data generating unit 41 includes an envelope detector 411 and a logarithmic converter 412. The envelope detector 411 detects each envelope of the receiving signals of M channels outputted from each of the receiving delay and summation units 223-1 to 223-M in the reception unit 22. The logarithmic converter 412 generates B mode data for the respective parallel simultaneous reception beam directions by emphasizing relative small amplitude signals of the envelope detected receiving signals.

The color Doppler data generating unit 42 includes a π/2 phase converter 421, mixers 422-1 and 422-2, and low pass filters (LPFs) 423-1 and 423-2. The color Doppler data generating unit 42 generates complex signals (I signal and Q signal) by performing orthogonal phase detection to each of the receiving signals outputted from the receiving delay and summation units 223-1 to 223-M in the reception unit 22.

The color Doppler data generating unit 42 further includes a Doppler signal memory unit 424, a MTI filter 425 of a high band pass digital filter and an auto-correlation computing unit 426. The Doppler signal memory unit 424 stores the complex signals acquired through the orthogonal phase detection. The MTI filter 425 reads the complex signals stored in the Doppler signal memory unit 424 and eliminates Doppler components (clatter components) in the complex signals due to influences of the movement of organs, such as movement due to breathing or heart beats. The auto-correlation computing unit 426 computes an auto-correlation value to the Doppler component in the extracted blood data and further generates color Doppler data for each of the parallel simultaneous reception beam directions by computing a mean flow value of the blood flow, a variance value, and a power value based on the auto-correlation value.

Figure 5:
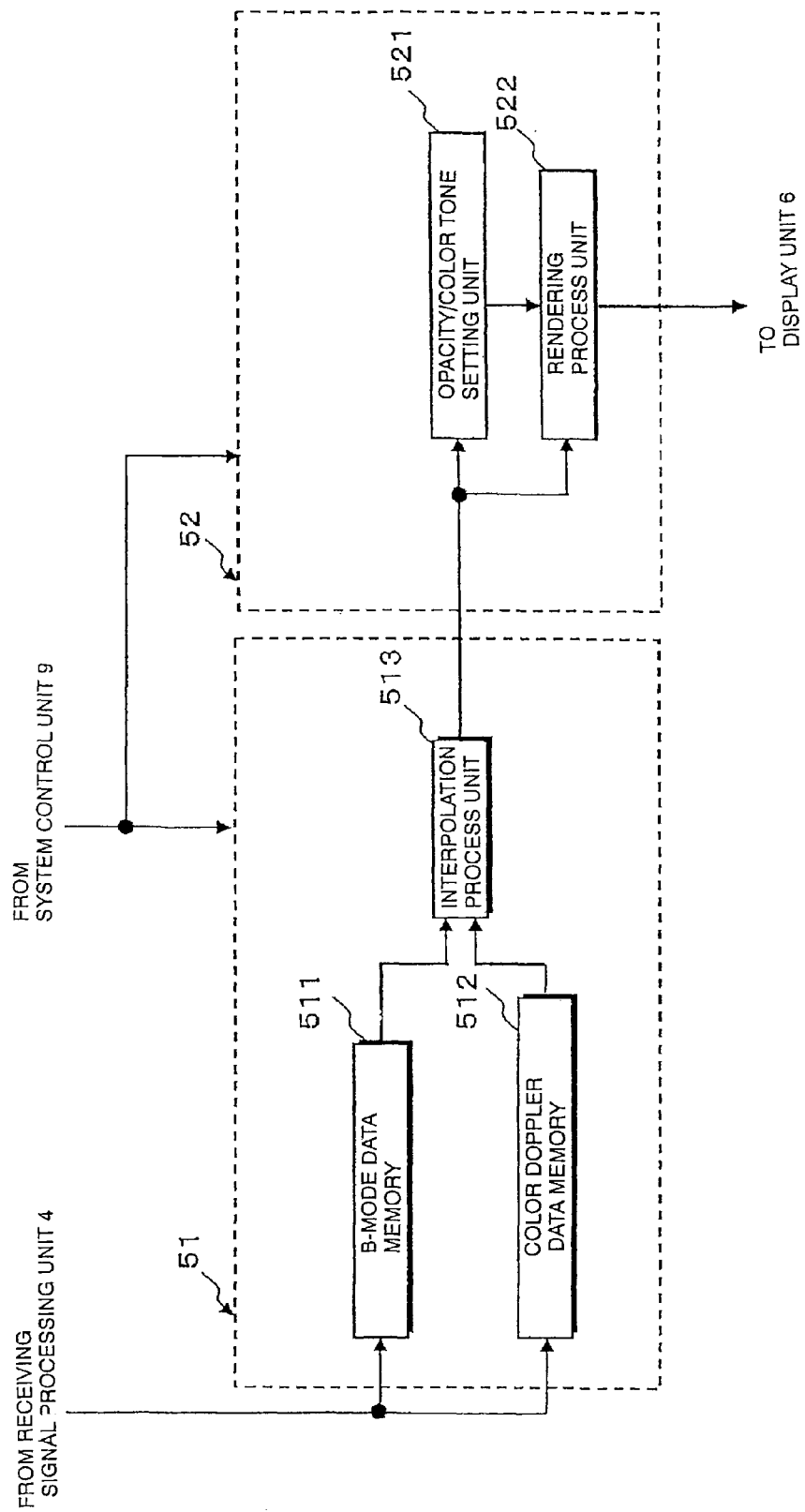
FIG. 5 a block diagram illustrating the image data generating unit in the ultrasound diagnosis apparatus shown in FIG. 1.

FIG. 5 illustrates construction of the 3D image data generating unit 5 in the ultrasound diagnosis apparatus shown in FIG. 1. The image data generating unit 5 includes a volume data generating unit 51 and a 3D image data generating unit 52. The volume data generating unit 51 includes a B mode data memory unit 511, a color Doppler data memory unit 512, and an interpolation process unit 513. The volume data generating unit 51 generates volume data based on the ultrasound data (B mode data and color Doppler data) supplied from the receiving signal processing unit 4. The 3D image data generating unit 52 includes an opacity/color tone setting unit 521 and a rendering process unit 522, and generates 3D image data by processing the generated volume data.

The B mode data memory unit 511 in the volume data generating unit 51 stores annex data of the reception beam directions and M channels of B mode data generated by the B mode data generating unit 41 in the receiving signals processing unit 4 based on the receiving signals that are acquired on an object by 3D scans by applying the M directions parallel simultaneous reception method as annex data of the ultrasound reception beam directions. Similarly, the color Doppler data memory unit 512 stores M channels of color Doppler data generated by the color Doppler data generating unit 42 based on the receiving signals beam directions.

The interpolation process unit 513 generates 3D B mode data by arranging the plurality of B mode data read out from the B mode data memory unit 511 in accordance with the reception beams directions, and further generates B mode data volume data comprised of isotopic voxels by performing an interpolation process to the 3D B mode data that is comprised of voxel data at unequal distances. The interpolation process unit 513, similarly, generates 3D color Doppler data by arranging a plurality of color Doppler data read out from the color Doppler data memory unit 512 in accordance with the reception beam directions and generates Doppler mode volume data by performing an interpolation process on the 3D color Doppler data.

The opacity/color tone setting unit 521 in the 3D image data generating unit 52 sets an opacity degree or color tone based on the voxel value of the B mode data or the Doppler mode data supplied from the interpolation process unit 513 in the volume data generating unit 51. The rendering process unit 522 generates 3D image data, such as volume rendering image data and surface rendering image data by performing rendering processes to the volume data, based on the opacity or the color tone data set by the opacity/color tone setting unit 521.

The display unit 6 (FIG. 1) includes a displaying data generating unit, a converting circuit, and a monitor (not shown). The displaying data generating unit performs coordinate conversions to the 3D image data generated by the 3D image data generating unit 52 in the image data generating unit 5 based on the eyes direction. Further, the displaying data generating unit generates displaying data by adding annex data, such as object data and image data generating conditions. The converting circuit performs D/A conversions and television format conversions to the displaying data generated in the displaying data generating unit in order to display the data on a monitor.

The input unit 7 is an interactive interface that includes a display panel and input devices, such as a keyboard, various switches, selection buttons, and a mouse. Various input operations, such as an input of the object data or image data generating conditions, and setting of image data displaying conditions, setting of eyes directions to the 3D image data, setting the beam number M for the parallel simultaneous reception, and inputs of various command signals are performed through the display panel and the input devices.

The scan control unit 8 controls 3D scans of the ultrasound probe 3 on the object based on the image data generating conditions and the beam number M for the parallel simultaneous reception inputted by the input unit 7. Practically, the scan control unit 8 sets the transmitting transducers group and the receiving transducers group based on the various setting conditions. Further, the scan control unit 8 sets the transmitting delay times, i.e., deflecting delay times and focusing delay times for the transmission, and receiving delay times, i.e., deflecting delay times and focusing delay times for the receptions that are necessary for the 3D scans by applying the M directions parallel simultaneous receptions to the transmission delay circuit 212 in the transmission unit 21 and the receiving delay and summation units 223-1 to 223-M in the reception unit 22.

The system control unit 9 includes a central processing unit (CPU) and a memory circuit (not shown). The memory circuit stores the above-mentioned various data that are inputted or set through the input unit 7. The CPU totally controls each unit in the ultrasound diagnosis apparatus 100 based on the input data and the set data so as to generate 3D image data (volume data) by the 3D scans applied with the parallel simultaneous reception.

Figure 6:
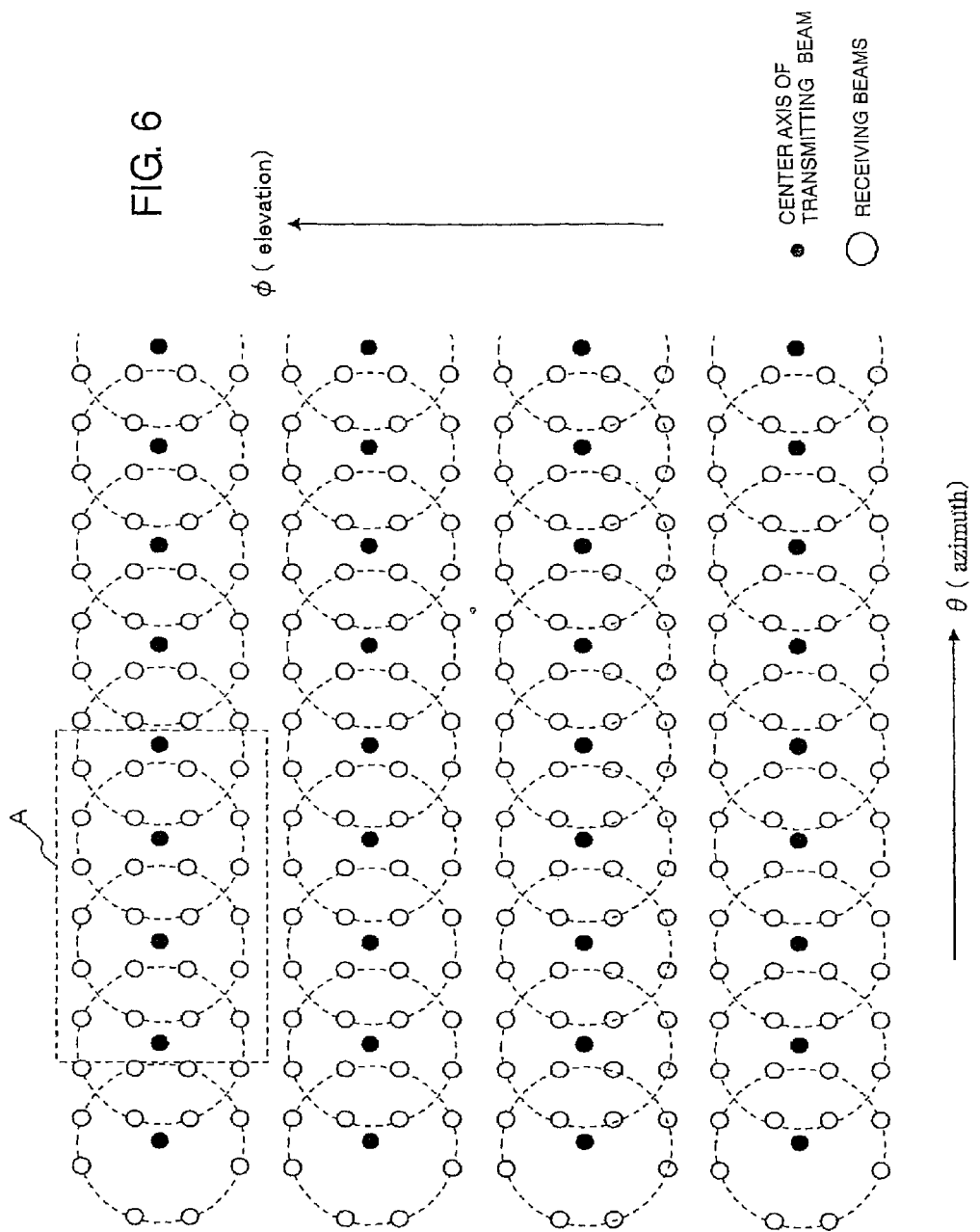
FIG. 6 illustrates an embodiment feature of the transmission beams and 8 direction parallel simultaneous reception beam directions corresponding to each of the transmission beam directions in the embodiment of the ultrasound diagnosis apparatus shown in FIG. 1.

FIG. 6 illustrates the parallel simultaneous reception method in the 3D scans by using an ultrasound probe 3 having 2D array transducers according to the ultrasound diagnosis apparatus consistent with embodiments of the present invention. In FIG. 6, the transversal axis indicates deflection angles to the $\theta$ (azimuth) direction, and the vertical axis indicates deflection angles to the $\phi$ (elevation) direction. In this embodiment, a transmitting acoustic field having a relatively wider beam width is set, and M (M=8) of reception beam directions, each having a uniformly thin beam width, are set at positions on a circle spaced apart a prescribed angular distance $\Delta\xi$ from a center axis (●) of the transmitting acoustic field. The set group of the transmitting acoustic field and the 8 parallel simultaneous reception beams is sequentially shifted by a prescribed angular distance $\Delta\xi_0$ along the $\theta$ (azimuth) direction and the $\phi$ (elevation) direction. By doing so, it becomes possible to acquire volume data having even transmission/reception sensitivity in the 3D region of the object in a short time.

Figure 7:
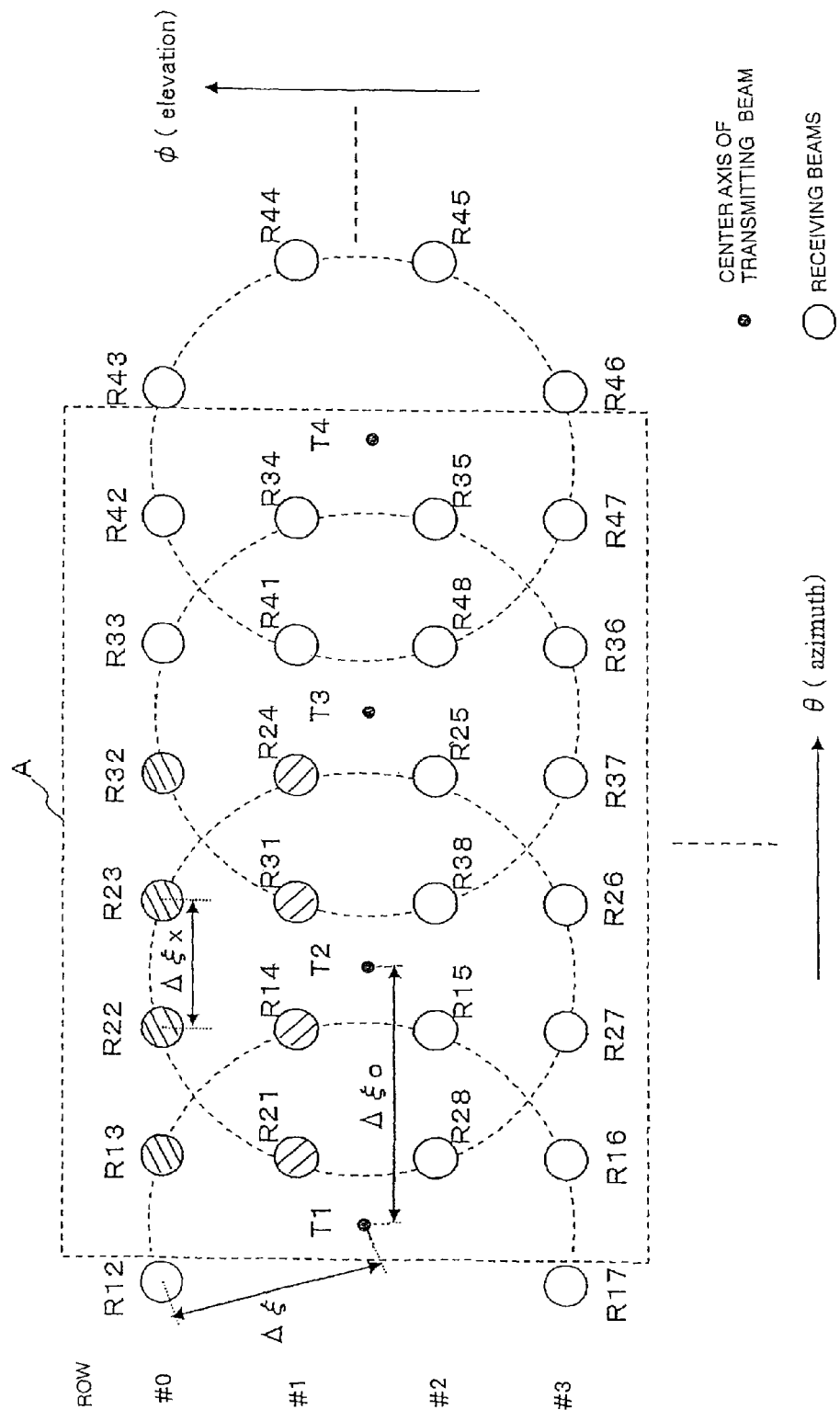
FIG. 7 illustrates how to set the transmission beams and the 8 direction parallel simultaneous reception beams shown in FIG. 6.

FIG. 7 is an enlarged view of the dotted region A shown in FIG. 6 for illustrating the parallel simultaneous reception method consistent with embodiments of the present invention. As illustrated in FIG. 7, in this embodiment, the number M of the simultaneous reception beams in the parallel simultaneous reception in the ultrasound transmitting acoustic field is set as 8 (M=8). Thus, 8 parallel simultaneous reception beams R11 to R18 (R12 to R17 only illustrated in FIG. 7) corresponded to the transmitting acoustic field T1 are set at the positions on a circle spaced apart by an angular distance $\Delta\xi$ from a center axis of the transmitting acoustic field T1. Thus, each of the 8 parallel simultaneous reception beams R11 to R18 is set at an equal angular distance $\Delta\xi$ from the center axis of the transmitting acoustic field T1. Similarly, 8 parallel simultaneous reception beams R21 to R28 are set on a circle centering a center axis of the transmitting acoustic field T2 that adjoins the transmitting acoustic field T1 in the $\theta$ (azimuth) direction by a prescribed angular distance $\Delta\xi_0$ so as to be spaced apart by angular distance $\Delta\xi$.

Similarly, the transmitting acoustic field T3 is set at a position of angular distance $\Delta\xi_0$ along the θ (azimuth) direction and 8 parallel simultaneous reception beams R31 to R38 corresponded to the transmitting acoustic field T3 are set on a circle centering the center axis of the transmitting acoustic field T3 by an angular distance $\Delta\xi$. Further, 8 parallel simultaneous reception beams R41 to R48 corresponded to a transmitting acoustic field T4 are set on a circle centering the center axis of the transmitting acoustic field T4 by an angular distance $\Delta\xi$. When the number M of the parallel simultaneous reception beams is selected, as shown in FIG. 7, each of the 8 parallel simultaneous reception beams can be set on a straight line at an equal angular distance $\Delta\xi x$ ($\Delta\xi x=\Delta\xi_0/2$) to the θ (azimuth) direction and the φ (elevation) direction. For instance, each of the parallel simultaneous reception beams R21, R14, R31, and R24 that are set so as to correspond to the 3 transmitting acoustic fields T1 to T3 on the same φ (elevation) direction (raw #1) are set at an equal angular distance $\Delta\xi x$.

Figure 8B:
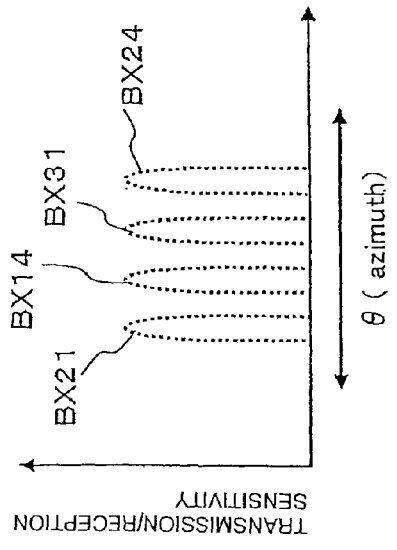
FIG. 8B illustrates the transmission/reception sensitivity distributions based on the transmission intensity distributions and the reception sensitivity distributions shown in FIG. 8A.
Figure 8D:
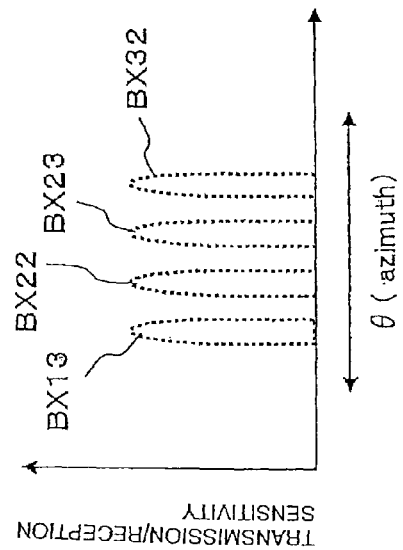
FIG. 8D illustrates the transmission/reception sensitivity distributions based on the transmission intensity distributions and the reception sensitivity distributions shown in FIG. 8C.
Figure 8A:
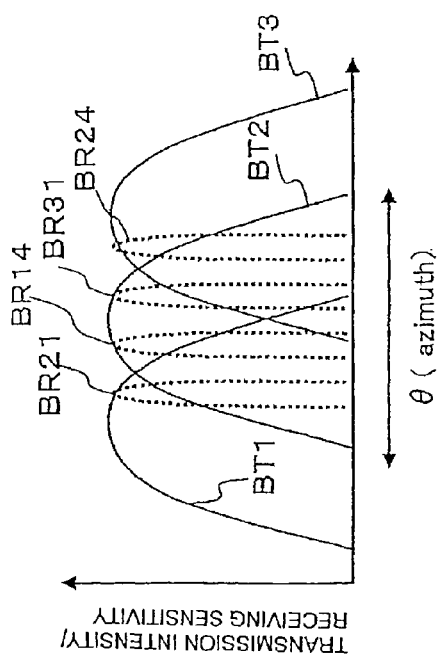
FIG. 8A illustrates the transmission intensity distributions (transmitting acoustic fields) for the transmission beams and reception sensitivity distributions (reception acoustic fields) corresponded to each of the transmission beams formed at the azimuth direction lines #1, #2 shown in FIG. 7.

FIGS. 8A-8D show the transmission intensity/reception sensitivity and the transmission/reception sensitivity in the embodiment of the 8 parallel simultaneous reception beams consistent with the present invention. FIG. 8A illustrates the transmission intensity distributions BT1 to BT3 formed by 3 transmitting acoustic fields T1 to T3, each having a relatively larger beam width and the reception sensitivity distribution BR21, BR14, BR31, and BR24 formed by the parallel simultaneous reception 4 beams R21, R14, R31, and R24 that are positioned on the same line #1 in a depth (azimuth) direction near to each center axis of the respective transmitting acoustic field among the parallel simultaneous reception beams being set to each of the transmitting acoustic fields T1 to T3.

FIG. 8B illustrates the transmission/reception sensitivity distributions BX21 based on the transmission intensity distribution BT1 and the reception sensitivity distribution BR21, the transmission/reception sensitivity distribution BX14 based on the transmission intensity distribution BT2 and the reception sensitivity distribution BR14, the transmission/reception sensitivity distribution BX31 based on the transmission intensity distribution BT2 and the reception sensitivity distribution BR31, and the transmission/reception sensitivity distribution BX 24 based on the transmission intensity distribution BT3 and the reception sensitivity distribution BR24. Since, each of the parallel simultaneous reception beam directions R21, R14, R31, and R24 is set at an equal angular distance $\Delta\xi x$ position apart from the transmitting acoustic field, equal transmission/reception sensitivity can be acquired to the parallel simultaneous reception beam directions R21, R14, R31, and R24.

Figure 8C:
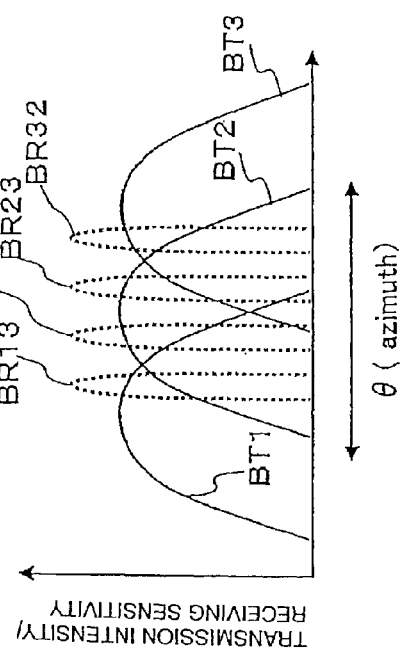
FIG. 8C illustrates the transmission intensity distributions (transmitting acoustic fields) for the transmission beams and reception sensitivity distributions (reception acoustic fields) corresponded to each of the transmission beams formed at the azimuth direction lines #0, #3 shown in FIG. 7.
Figure 9:
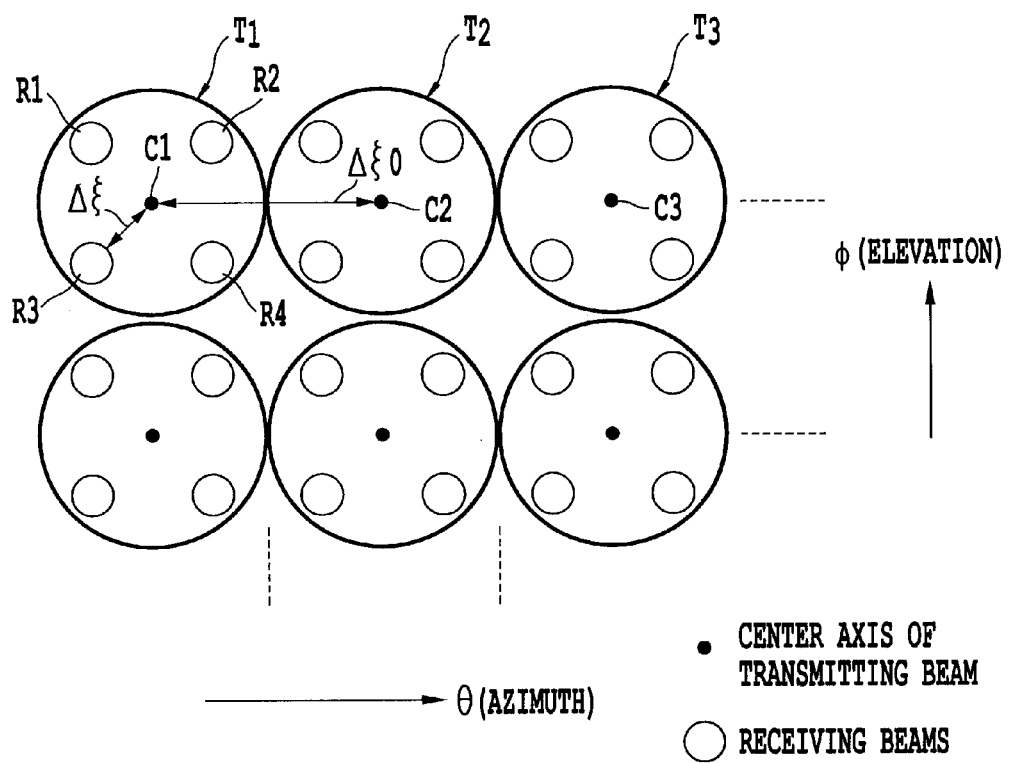
FIG. 9 illustrates a background art of the 4-beams parallel simultaneous reception method by using a 2D array ultrasound probe.
Figure 10:
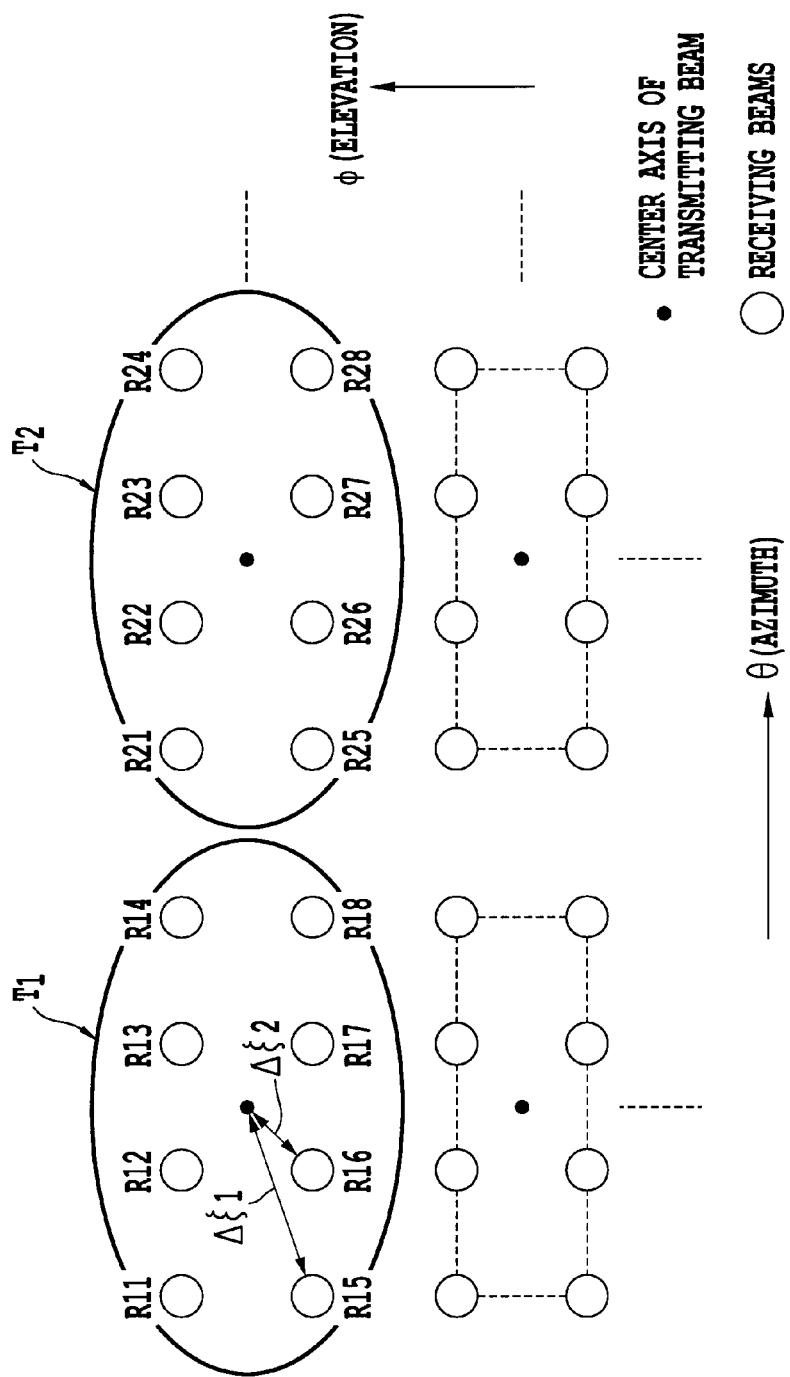
FIG. 10 illustrates a hypothetical 8-beams parallel simultaneous reception model by applying the background art.

Similarly, FIG. 8C illustrates the transmission intensity distributions BT1 to BT3 formed by the transmitting acoustic field T1 to T3, and the reception sensitivity distributions BR13, BR22, BR23, and BR32 formed by the parallel simultaneous reception 4 beams R13, R22, R23, and R32 on the row #0 position in the azimuth direction that locate a far distance from the center axis of the transmitting acoustic fields T1 to T3. FIG. 8D illustrates the transmission/reception sensitivity distribution BX13 based on the transmission intensity distribution BT1 and the reception sensitivity distribution BR13, the transmission/reception sensitivity distribution BX22 based on the transmission intensity distribution BT2 and the reception sensitivity distribution BR22, the transmission/reception sensitivity distribution BX23 based on the transmission intensity distribution BT2 and the reception sensitivity distribution BR23, and the transmission/reception sensitivity distribution BX32 based on the transmission intensity distribution BT3 and the reception sensitivity distribution BR32.

In this case, each of the parallel simultaneous reception 4 beam directions R13, R22, R23, and R32 is set apart from the transmitting acoustic field corresponded to these parallel simultaneous reception beam by an equal angular distance $\Delta\xi$. Accordingly, an equal transmission/reception sensitivity is acquired to the parallel simultaneous reception beams R13, R22, R23, and R32. Further, these transmission/reception sensitivities becomes equal to the transmission/reception sensitivity for the parallel simultaneous reception beams R21, R14, R31, and R24 shown in FIG. 8B.

Thus, the above-mentioned parallel simultaneous receptions are successively repeated by centering on each of transmission beam directions set by angular distance $\Delta\xi_0$ on the θ (azimuth) direction and the φ (elevation) direction. By doing so, a 3D scan to the object is performed.

According to an embodiment consistent with the present invention, it becomes possible to reduce the deterioration of the transmission/reception sensitivity and the unevenness by setting more than 5 parallel simultaneous reception beam directions at an equal angular distance from the center axis of the transmission beam directions. Consequently, the system according to an embodiment of the invention can acquire 3D image data of a superior quality in real time.

In particular, when 8 parallel simultaneous reception beams are set for one transmission beam direction, since the parallel simultaneous reception beam directions having a prescribed of angular distance $\Delta\xi$ to the transmission beam direction can be set at a prescribed angular distance $\Delta\xi x$ on the orthogonally crossing 2 directions (θ direction and φ direction), it becomes possible to generate volume data of a good quality.

Of course, the present invention is not limited to the above embodiments. For instance, the invention is applicable to the parallel simultaneous reception in a linear scan type ultrasound diagnosis apparatus or a convex scan type ultrasound diagnosis apparatus. In the embodiment of the parallel simultaneous reception for the sector scan type ultrasound diagnosis apparatus, each of the parallel simultaneous reception beam directions is set at a prescribed angular distance $\Delta\xi$ to the transmission beam direction. In the parallel simultaneous reception in a linear scan type ultrasound diagnosis apparatus or a convex scan type ultrasound diagnosis apparatus, each of the parallel simultaneous reception beam directions may set at a prescribed distance interval to the transmission beam direction.

In the above-mentioned embodiment, 8 parallel simultaneous reception beam directions are set to one transmission beam direction. Of course, the number of the parallel simultaneous reception beam is only limited so as to be more than five. However, if the number other than eight (8) is set as the parallel simultaneous reception beams, the volume data acquisition speed (volume rate) is not always proportioned to an inverse number of the parallel simultaneous reception beams, since a plurality of parallel simultaneous receptions may be performed to the same reception beam direction.

In the above-mentioned embodiment, the 3D image data is generated based on the volume data acquired through 3D scans on the object. It is, of course, possible to generate maximum intensity projection (MIP) image data or multi-planar reconstruction (MPR) image data.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

What is claimed is:

1. An ultrasound diagnosis apparatus configured to generate three-dimensional (3D) ultrasound image data based on ultrasound receiving signals acquired through 3D scans using a parallel simultaneous reception method, the ultrasound diagnosis apparatus comprising:
a processor configured to cause a scan controller to set an ultrasound transmitting acoustic field and a plurality of parallel simultaneous reception beam directions corresponding to a center axis of the transmitting acoustic field and to perform the 3D scans by sequentially shifting the transmitting acoustic field and the plurality of parallel simultaneous reception beam directions corresponding to the transmitting acoustic field along a prescribed direction;
an ultrasound probe including a plurality of two-dimensional (2D) array transducers;
a transmission circuit configured to emit ultrasound transmission beams by driving the plurality of transducers;
a reception circuit configured to perform parallel simultaneous reception of the ultrasound receiving signals of a plurality of channels acquired through each of the plurality of parallel simultaneous reception beam directions by delaying and summing, respectively; and
an image data generating processor configured to generate the 3D ultrasound image data based on the delayed and summed ultrasound receiving signals acquired from each of the parallel simultaneous reception beam directions that are sequentially shifted in the prescribed direction,
wherein the processor is further configured to cause the scan controller to set, as the plurality of parallel simultaneous reception beam directions, exactly eight parallel simultaneous reception beam directions,
all of the set plurality of parallel simultaneous reception beam directions corresponding to the transmitting acoustic field are equally spaced with a same pitch in each of two orthogonal directions by shifting the parallel simultaneous reception beam directions, and
the processor is configured to cause the scan controller to shift the transmitting acoustic field by an amount equal to twice the pitch between the reception beam directions.

2. The ultrasound diagnosis apparatus according to claim 1, wherein the processor is configured to cause the scan controller to set the parallel simultaneous reception beam directions so that the reception beam directions acquired through the 3D scan are equally spaced in four rows by shifting the parallel simultaneous reception acoustic fields.

3. The ultrasound diagnosis apparatus according to claim 1, wherein the image data generating processor generates volume data based on the delayed and summed ultrasound receiving signals and generates at least one of 3D image data of maximum intensity projection (MIP) image data and 3D image data of multiplanar reconstruction (MPR) image data by processing the volume data.

4. The ultrasound diagnosis apparatus according to claim 1, further comprising:
a display configured to display the image data generated by the image data generating processor in real time.

5. An ultrasound diagnosis apparatus configured to generate image data based on ultrasound receiving signals acquired through 3D scans using a parallel simultaneous reception method, the ultrasound diagnosis apparatus comprising:
a processor configured to cause a scan controller to set an ultrasound transmitting acoustic field and exactly eight parallel simultaneous reception beam directions, wherein all of the eight parallel simultaneous reception beam directions are spaced apart at non-uniform angles on a circle around the center axis of the ultrasound transmitting acoustic field, and to perform the 3D scans by sequentially shifting the transmitting acoustic field and the parallel simultaneous reception beam directions in a prescribed direction;
an ultrasound probe including a plurality of 2D array transducers;
a transmission circuit configured to emit transmission ultrasounds for forming the transmitting acoustic field by driving the plurality of transducers;
a reception circuit configured to achieve parallel simultaneous reception by delaying and summing the ultrasound receiving signals of a plurality of channels acquired from each of the parallel simultaneous reception beam directions; and
an image data generating processor configured to generate the image data based on the delayed and summed ultrasound receiving signals acquired from each of the parallel simultaneous reception beam directions sequentially shifted to the prescribed direction,
wherein the scan processor is further configured to cause the scan controller to set the parallel simultaneous reception beam directions that are acquired through the 3D scan around a transmission beam direction so that the reception beam directions are equally spaced with a same pitch in each of two orthogonal directions, by shifting the parallel simultaneous reception beam directions; and
the processor is configured to cause the scan controller to shift the transmitting acoustic field by an amount equal to twice the pitch between the reception beam directions.

6. The ultrasound diagnosis apparatus according to claim 5, wherein the image data generating processor generates volume data based on the delayed and summed ultrasound receiving signals and generates at least one of 3D image data of MIP image data and 3D image data of multi-planar reconstruction (MPR) image data by processing the volume data.

7. The ultrasound diagnosis apparatus according to claim 5, further comprising:
a display configured to display the image data generated by the image data generating processor in real time.

* * * * *